US008998954B2

(12) United States Patent
Hartsell et al.

(10) Patent No.: US 8,998,954 B2
(45) Date of Patent: Apr. 7, 2015

(54) SPINOUS PROCESS SPACER

(75) Inventors: Brian D. Hartsell, Aurora, IL (US); Kara A. Bucci, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 318 days.

(21) Appl. No.: 12/848,581

(22) Filed: Aug. 2, 2010

(65) Prior Publication Data

US 2011/0029021 A1 Feb. 3, 2011

Related U.S. Application Data

(60) Provisional application No. 61/230,794, filed on Aug. 3, 2009.

(51) Int. Cl.
*A61B 17/70* (2006.01)
*A61F 2/44* (2006.01)
*A61F 2/30* (2006.01)

(52) U.S. Cl.
CPC ... *A61B 17/7065* (2013.01); *A61F 2002/30179* (2013.01)

(58) Field of Classification Search
USPC ............... 606/246–249; 623/17.11–17.16
See application file for complete search history.

(56) References Cited

U.S. PATENT DOCUMENTS

| | | | |
|---|---|---|---|
| 5,226,767 A * | 7/1993 | Foerster, Jr. | 411/340 |
| 5,390,683 A | 2/1995 | Pisharodi | |
| 5,658,335 A | 8/1997 | Allen | |
| 5,658,337 A | 8/1997 | Kohrs et al. | |
| 6,126,689 A | 10/2000 | Brett | |
| 6,176,882 B1 | 1/2001 | Biedermann et al. | |
| 6,375,682 B1 | 4/2002 | Fleischmann et al. | |
| 6,409,766 B1 | 6/2002 | Brett | |
| 6,491,724 B1 | 12/2002 | Ferree | |
| 6,494,883 B1 | 12/2002 | Ferree | |

(Continued)

FOREIGN PATENT DOCUMENTS

WO WO-2006/105437 10/2006

OTHER PUBLICATIONS

Written Opinion of the International Searching Authority for Application No. PCT/US10/44223, date of mailing Sep. 17, 2010, 5 pages.

*Primary Examiner* — Mary Hoffman
*Assistant Examiner* — Michelle C Eckman
(74) *Attorney, Agent, or Firm* — Foley & Lardner LLP

(57) ABSTRACT

A spinous process spacer that is designed to maintain a desired spatial relationship between adjacent vertebrae, is configured for introduction into a spinal implant site in a compressed state and then expands in situ. Once expanded, formations of the present spinal spacer form areas, pockets or spaces that receive at least one bony portion of each adjacent vertebra. The present spinous process spacer has a changeable circumferential profile wherein a first circumferential profile is smaller than a second circumferential profile in order to provide/achieve its compressed and expanded states. The first circumferential profile defines the collapsed position or state while the second circumferential profile defines the position or state. Upon implantation, the present spinous process spacer is not fixed to any bony structure of the vertebrae but provides support. In this regard, use of the spinous process spacer, by itself, will not result in vertebral fusion. However, fusion can result with the use of bone graft packed about the spinous processes (and the spinous process spacer) or in conjunction with the use of an intervertebral body spacer.

14 Claims, 7 Drawing Sheets

(56) References Cited

U.S. PATENT DOCUMENTS

| | | | |
|---|---|---|---|
| 6,537,320 | B1 | 3/2003 | Michelson |
| 6,648,917 | B2 | 11/2003 | Gerbec et al. |
| 6,773,460 | B2 | 8/2004 | Jackson |
| 7,087,055 | B2 | 8/2006 | Lim et al. |
| 7,344,564 | B2 | 3/2008 | Sweeney |
| 7,731,751 | B2 | 6/2010 | Butler et al. |
| 7,811,331 | B2 * | 10/2010 | Johnson et al. ............ 623/17.16 |
| 2004/0153156 | A1 | 8/2004 | Cohen et al. |
| 2004/0167625 | A1 | 8/2004 | Beyar et al. |
| 2005/0033437 | A1 | 2/2005 | Bao et al. |
| 2005/0131536 | A1 | 6/2005 | Eisermann et al. |
| 2005/0143827 | A1 | 6/2005 | Globerman et al. |
| 2005/0228391 | A1 | 10/2005 | Levy et al. |
| 2006/0084988 | A1 * | 4/2006 | Kim ................................ 606/61 |
| 2006/0085070 | A1 * | 4/2006 | Kim ......................... 623/17.11 |
| 2006/0095136 | A1 | 5/2006 | McLuen |
| 2006/0189999 | A1 | 8/2006 | Zwirkoski |
| 2006/0224241 | A1 * | 10/2006 | Butler et al. ............... 623/17.15 |
| 2009/0112318 | A1 * | 4/2009 | Butler et al. ............... 623/16.11 |
| 2009/0198337 | A1 * | 8/2009 | Phan ......................... 623/17.16 |
| 2009/0240335 | A1 * | 9/2009 | Arcenio et al. ............ 623/17.16 |
| 2009/0306715 | A1 * | 12/2009 | Jackson et al. ................ 606/249 |
| 2010/0174373 | A1 * | 7/2010 | Galley et al. .............. 623/17.13 |
| 2010/0222816 | A1 * | 9/2010 | Gabelberger et al. ......... 606/249 |
| 2010/0305705 | A1 | 12/2010 | Butler et al. |
| 2011/0035011 | A1 * | 2/2011 | Cain ......................... 623/17.16 |

\* cited by examiner

SPINOUS PROCESS SPACER

RELATED APPLICATIONS

This patent application claims the benefit of and/or priority under 35 U.S.C. §119(e) to U.S. Provisional Patent Application Ser. No. 61/230,794 filed Aug. 3, 2009, entitled "Spinous Process Spacer" the entire contents of which is specifically incorporated herein by this reference.

BACKGROUND OF THE INVENTION

1. Field of the Invention

The present invention relates to devices for the spine and, more particularly, to a spinal implant for the treatment of stenotic spinal bone.

2. Background Information

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as lumbar spinal stenosis. Lumbar spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of lumbar spinal stenosis include leg pain ("pins and needles") that can limit standing, walking, self-supporting daily activities, work, social and recreational pursuits. Lack of activity because of lumbar spinal stenosis may lead to obesity, depression and general physical deterioration.

Once diagnosed with lumbar spinal stenosis the doctor will usually try non-surgical treatments first. Such treatments may include anti-inflammatory medications (orally or by injection) to reduce associated swelling or analgesic drugs to control pain. Physical therapy may be prescribed with goals of improving ones strength, endurance and flexibility so that you can maintain or resume a more normal lifestyle. Spinal injections such as an epidural injection of cortisone may also be used. Such non-surgical treatments do not correct the spinal canal narrowing of lumbar spinal stenosis itself but may provide long-lasting pain control and improved life function without requiring a more invasive treatment. However, as a last resort for those patients who don't respond to non-surgical treatments, surgery will be advised.

Lumbar spinal stenosis is the most common reason for back surgery in people over the age of 50 in the United States. While there are various non-surgical treatments for lumbar spinal stenosis, a surgical procedure known as a laminectomy may be performed in order to reduce or eliminate the symptoms of lumbar spinal stenosis. A laminectomy or lumbar decompression surgery has the goal of opening up the bony canal to improve available space for the spinal nerves. As indicated, however, a laminectomy is usually a last resort for treating lumbar spinal stenosis. This is because a laminectomy is an invasive surgical procedure.

Fortunately, another surgical treatment for lumbar spinal stenosis is known that is less invasive than a laminectomy. This other surgical treatment involves implanting a spinal spacer between bony projections of adjacent vertebrae, particularly, but not necessarily, between spinous processes of adjacent vertebrae. It can be appreciated that the more compact the spinal spacer, the less invasive the surgical implantation procedure.

In view of the foregoing, it is therefore desirable to provide a compact spinal spacer. Moreover, it is desirable to provide a spinal spacer that is compact during implantation and expandable in situ.

SUMMARY OF THE INVENTION

A spinal implant, spinal spacer or stenotic device for maintaining a desired spatial relationship between adjacent vertebrae is provided that is configured for introduction into a spinal implant site in a compressed, collapsed, compacted or un-expanded state and then expands, un-compacts, or un-compresses in situ. Once expanded, formations of the present spinal spacer form areas, pockets or spaces that receive at least one bony portion of each vertebra.

The present spinal implant is embodied as a bony spinal protrusion spacer, spinous process spacer, interlaminar spacer, or inter-joint spacer (collectively, "spinous process spacer") that is configured to be received in and fit between at least one bony spinal protrusion, of adjacent vertebrae of the spine and hold them apart. The present spinous process spacer may be made of titanium, PEEK, bone, a biocompatible elastomeric or other biocompatible material or compound.

Upon implantation, the present spinous process spacer is not fixed to any bony structure of the vertebrae but provides support. In this regard, use of the spinous process spacer, by itself, will not result in vertebral fusion. However, fusion can result with the use of bone graft packed about the spinous processes (and the spinous process spacer) or in conjunction with the use of an intervertebral body spacer.

The present spinous process spacer has a changeable circumferential profile wherein a first circumferential profile is smaller than a second circumferential profile in order to provide/achieve its compressed and expanded states. The first circumferential profile defines the collapsed, compressed, un-expanded or compacted position or state (compressed position) while the second circumferential profile defines an expanded, un-compressed, un-compacted position or state (expanded position).

In one form, the present spinous process spacer comprises a plurality of plates, each plate having a plurality of hinged flanges. When the flanges are folded, the spinous process spacer is in the compressed position. When the flanges are unfolded, the spinous process spacer is in the expanded position.

In a particular form, each plate defined by a center, core or central plate portion with a plurality of hinged flanges, protrusions, petals or leafs (collectively, 'flanges'). The spinal spacer is thus formed of a stack of plates wherein flanges of one plate register with flanges of an adjacent plate to collectively form legs. The flanges fold or bend relative to the core.

Unlike decompressive surgery/laminectomy, the procedure for implanting the present spinal spacer is completely reversible, leaving all anatomical structures intact. Thus, the implantation procedure for the present spinal spacer can be used as a first line surgical approach without compromising any therapeutic alternatives, including laminectomy.

Because extension (e.g. standing upright) provokes spinal stenosis symptoms, the present spinal spacer is designed to impose what is referred to as acute kyphosis of the lumbar spine. This kyphosing of the vertebral bodies opens the foramen (of which are usually stenotic in the elderly) and allows the nerves to move a little more. Inserted through a small incision, the present spinal spacer is preferably placed posterior to neural structures to minimize the risk of neural injury. Other manners of implantation may be used.

This is a minimally invasive procedure whereby the compressed process spinal spacer is inserted into the space between adjacent bony spinal protrusions to provide localized distraction to the lamina. Once positioned, compressed flanges are expanded to provide an "X" shaped body. Legs of the X-shaped body allow receipt of the bony spinal protrusions.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A discussion of the features, functions and/or configurations of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE INVENTION

Figure 1:
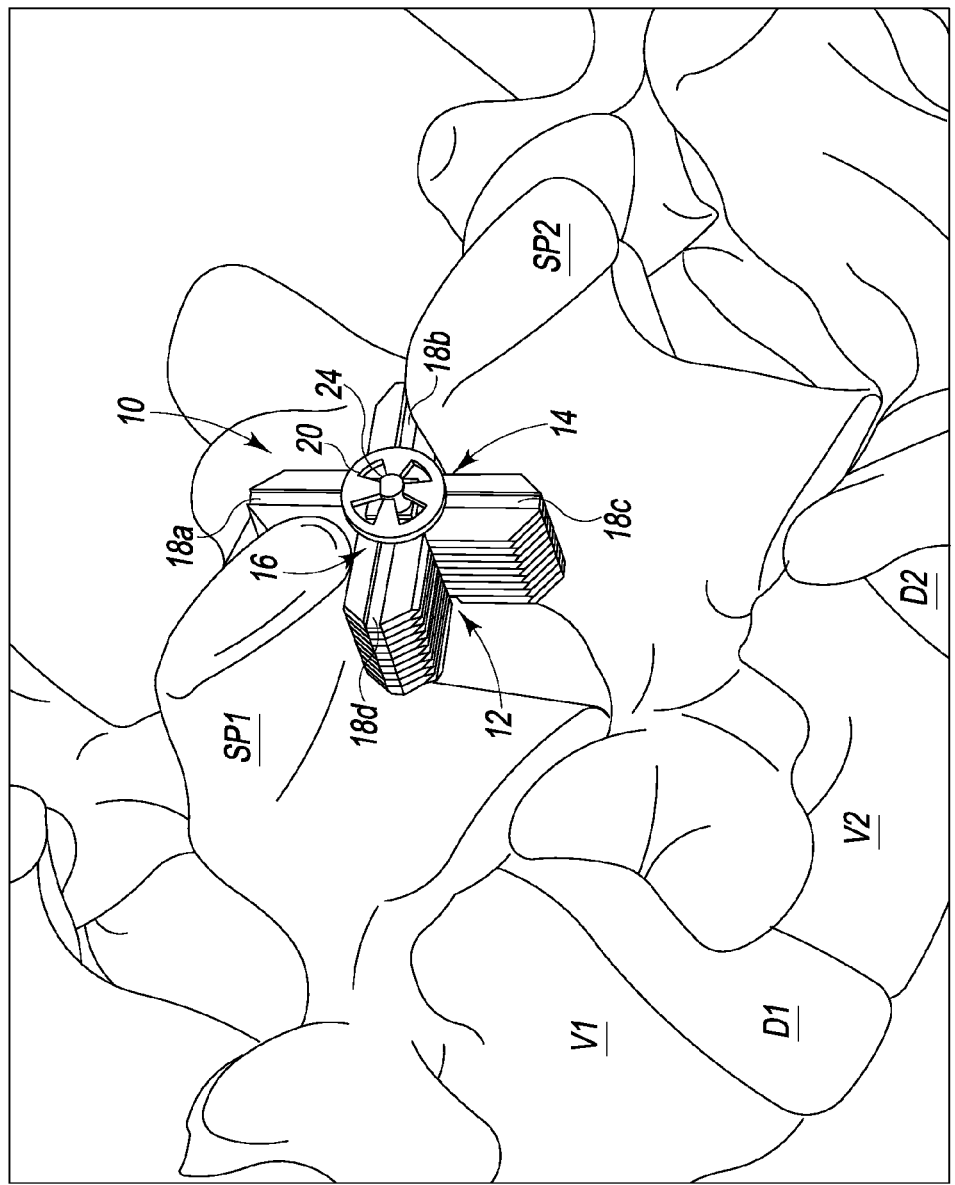
FIG. 1 is an isometric view of a portion of a human spine having a spinous process spacer fashioned in accordance with the principles of the present invention implanted between spinous processes of adjacent vertebrae.
Figure 2:
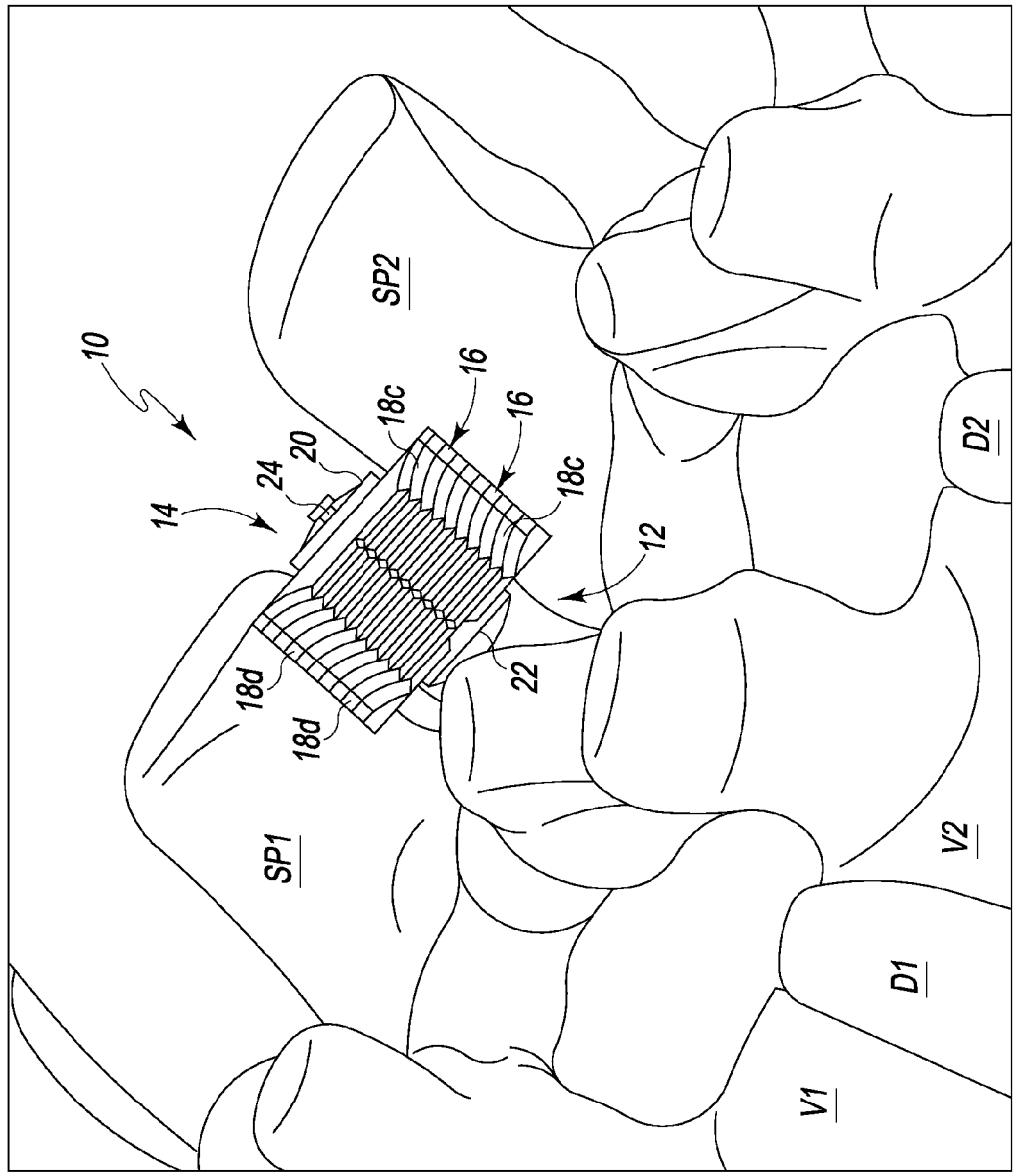
FIG. 2 is an enlarged lateral view of the implanted spinous process spacer of FIG. 1.
Figure 3:
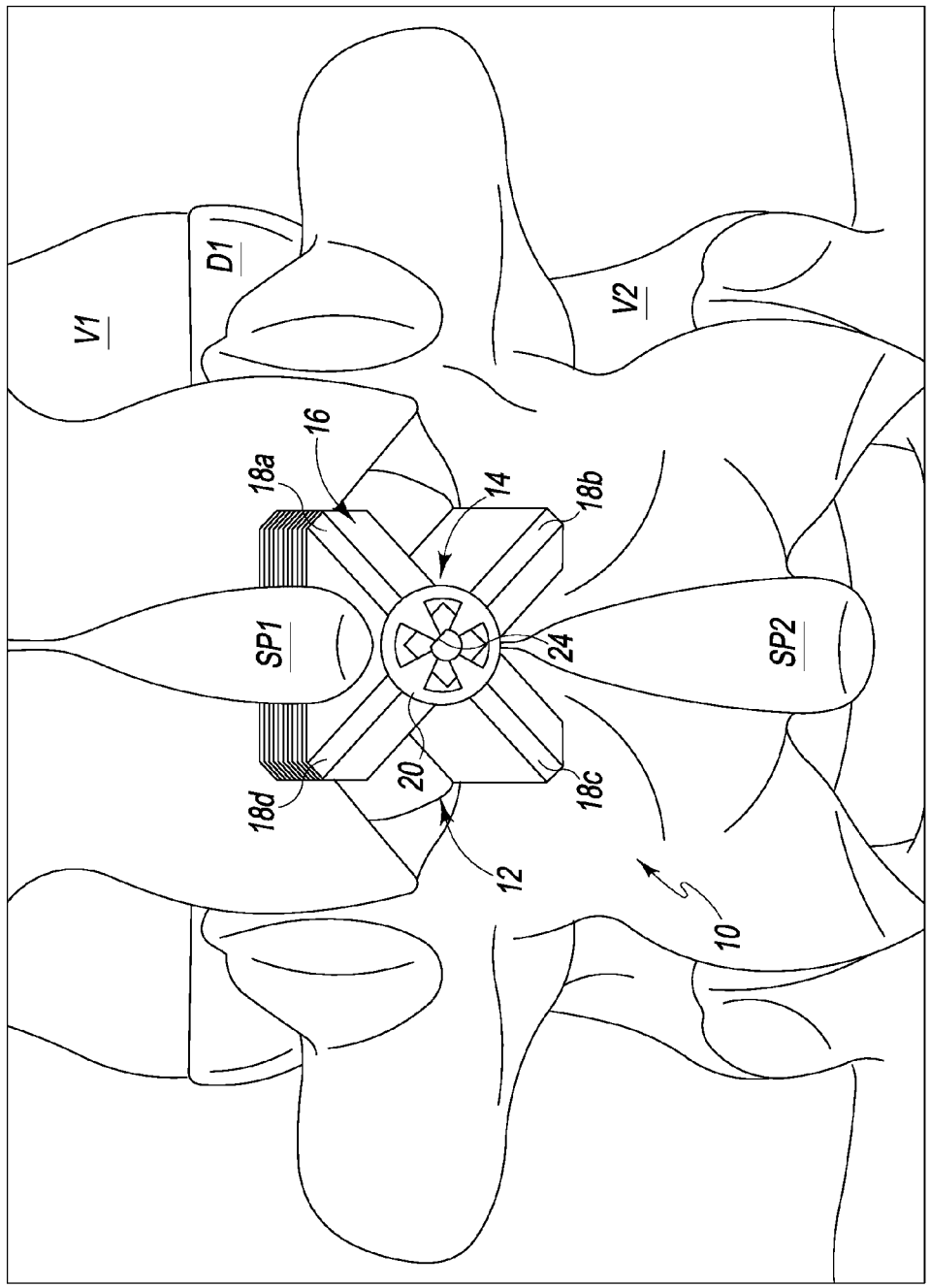
FIG. 3 is a posterior view of the implanted spinous process spacer of FIG. 1.
Figure 4:
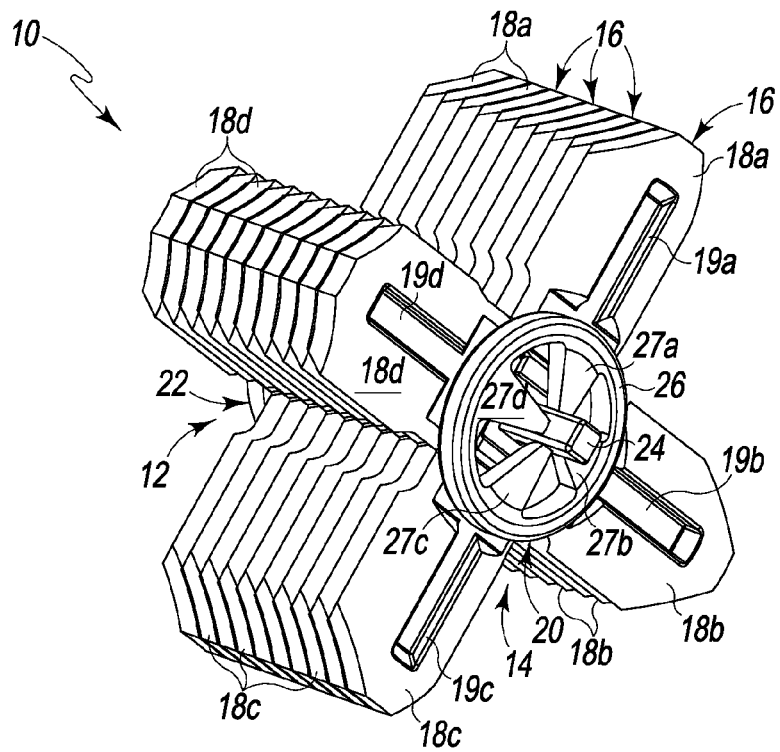
FIG. 4 is a front perspective view of the present spinous process spacer.
Figure 5:
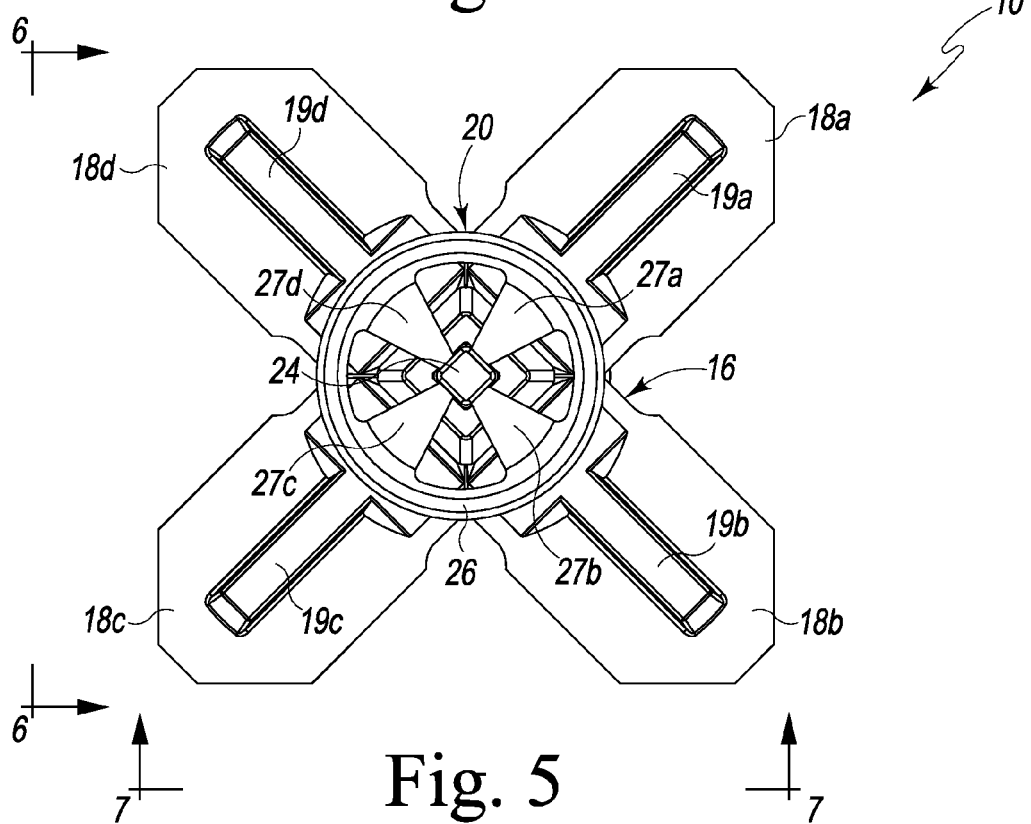
FIG. 5 is a posterior plan view of the present spinous process spacer.
Figure 6:
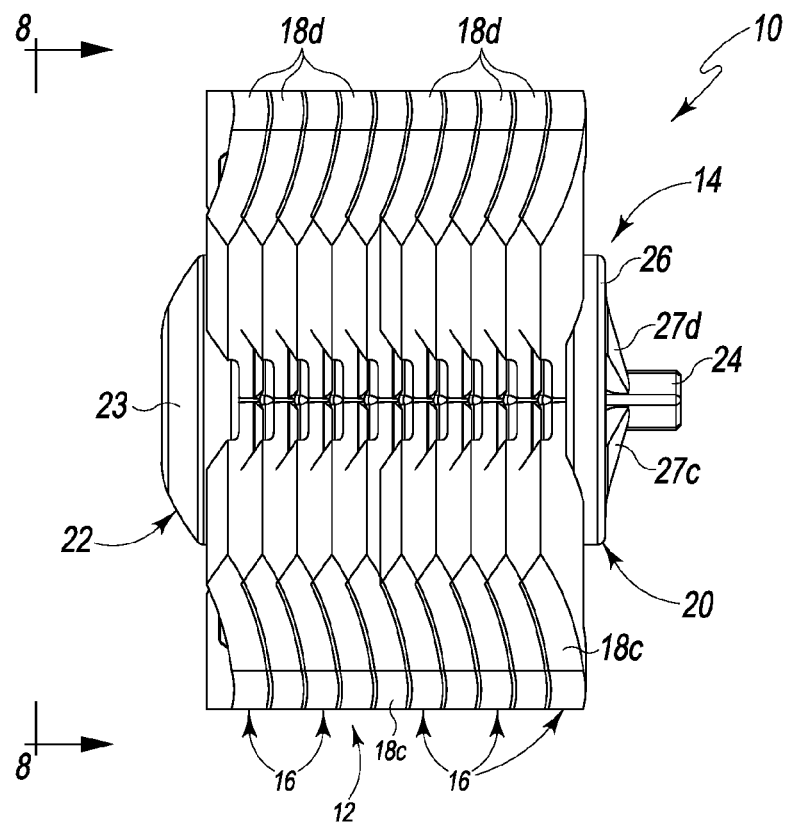
FIG. 6 is a side view of the present spinous process spacer taken along line 6-6 of FIG. 5.
Figure 7:
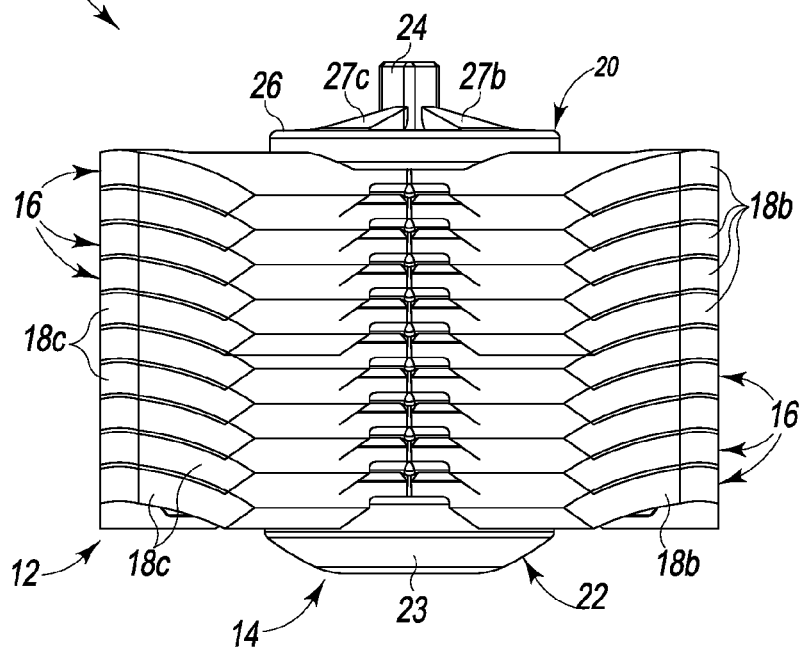
FIG. 7 is a side view of the present spinous process spacer taken along line 7-7 of FIG. 5.
Figure 8:
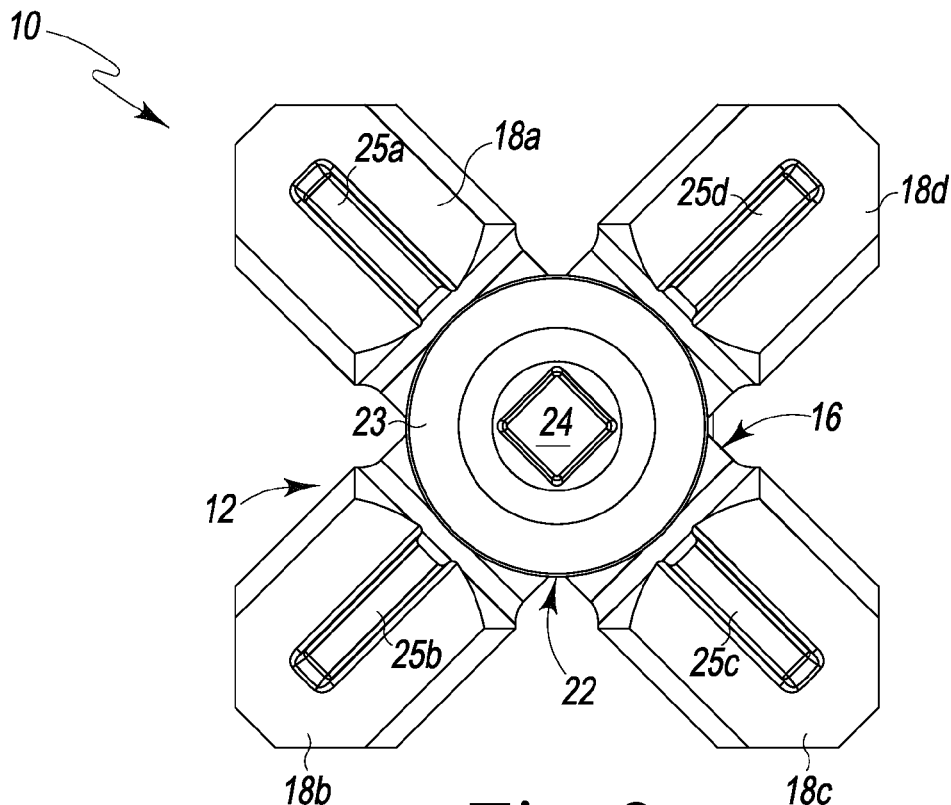
FIG. 8 is an anterior view of the present spinous process spacer.

FIGS. 1 through 3 depict a portion of a human spine wherein a spinous process spacer 10, fashioned in accordance with the present principles, has been implanted between bony protrusions of adjacent vertebrae. Particularly, there is depicted adjacent vertebra V1 and V2 of a portion of the spine, with a spine disc D1 situated between the vertebrae. Vertebra V1 has a spinous process SP1 and vertebra V2 has a spinous process SP2. The spinous process spacer 10 is shown situated between the spinous processes SP1 and SP2 of respective adjacent vertebrae V1 and V2 in the expanded position. It should be appreciated that while the present spinal process spacer 10 is shown situated between spinal processes SP1 and SP2, the present spinal process spacer 10 may be used as an interlaminar, interbody, or interbony spinal protrusion spacer. As such, while the present spinal process spacer 10 is shown and described in relation to the spinal processes of adjacent vertebrae, the spinal process spacer may be used between relevant bony structures of the vertebrae. It should thus be appreciated that while the present spinal process spacer 10 is shown and described with respect to the spinous process, the spinous process spacer may be used with other bony structures, the spinous process being only exemplary.

The spinal process spacer 10 is made from a biocompatible material such as titanium. Other biocompatible materials or compounds may be used such as PEEK, bone or an elastomeric. The spinal process spacer 10 is configured and/or adapted to receive, hold and maintain a desired spacing between adjacent vertebrae V1, V2 (and spinous processes SP1, SP2) and this is accomplished by receipt of the spinous process spacer 10 between the spinous process SP1 and spinous process SP2. The spacing is defined by the dimensions of the spinal process spacer 10. As such, the spinal process spacer 10 may be made in various sizes or dimensions to accommodate various anatomies.

The spinous process spacer 10 has a body 12 formed of a plurality of individual plates 16 held together by a carrier/expansion assembly 14. The carrier assembly 14 includes a top or first end cap 20, a bottom or second end cap 22, and a post 24, the nomenclature top, bottom, first and second being arbitrary. The stack of plates 12 is held onto the post 24 between the bottom end cap 22 and the top end cap 20. Each plate 16 has four (4) flanges 18a, 18b, 18c and 18d extending from a base 32 (see, e.g., FIG. 9). A stack of flanges defines a leg. As seen in the figures, the four (4) stacks of flanges are situated about the cores 32 so as to define four (4) legs in an 'X' configuration. Other configurations are contemplated.

Figure 9:
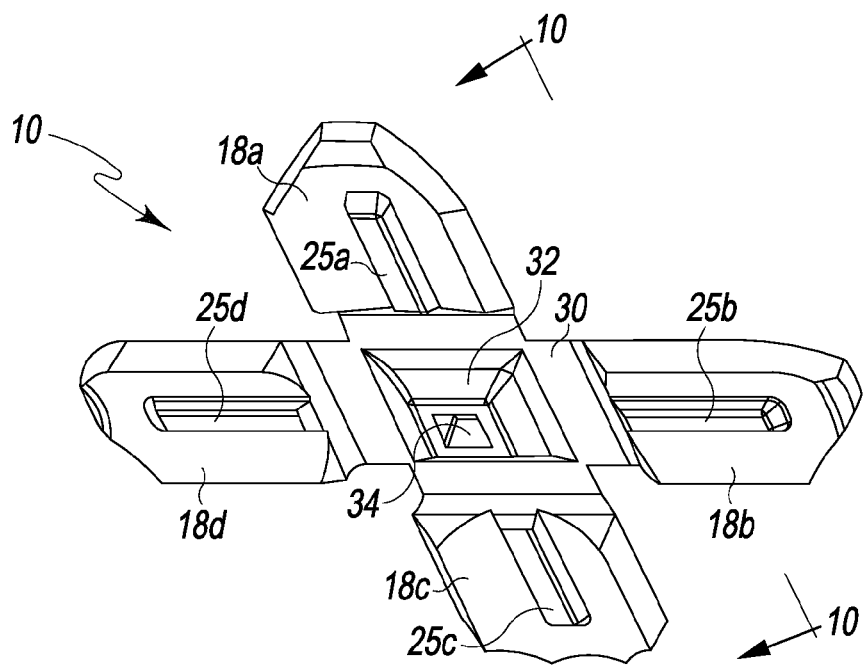
FIG. 9 is a bottom perspective view of a plate component of the present spinous process spacer.
Figure 10:
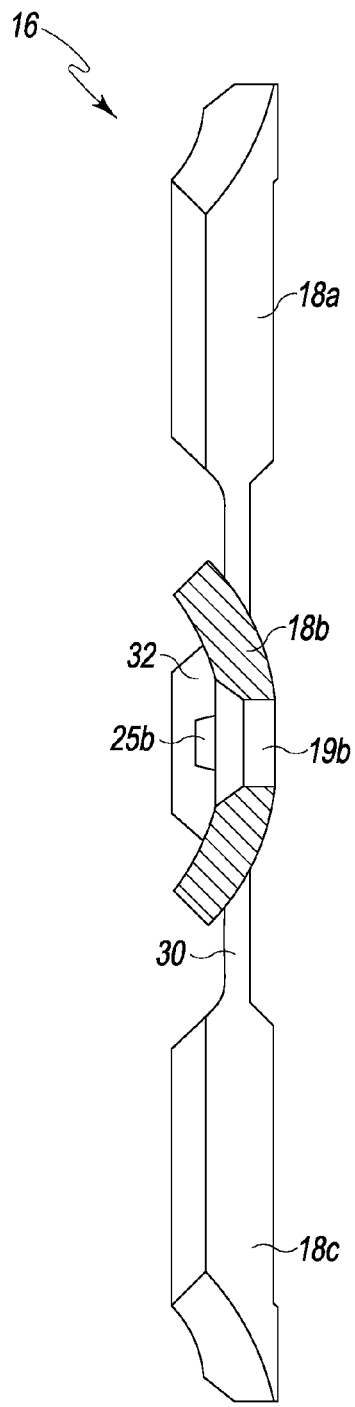
FIG. 10 is a sectional view of the plate component of FIG. 9 taken along line 10-10 thereof.
Figure 11:
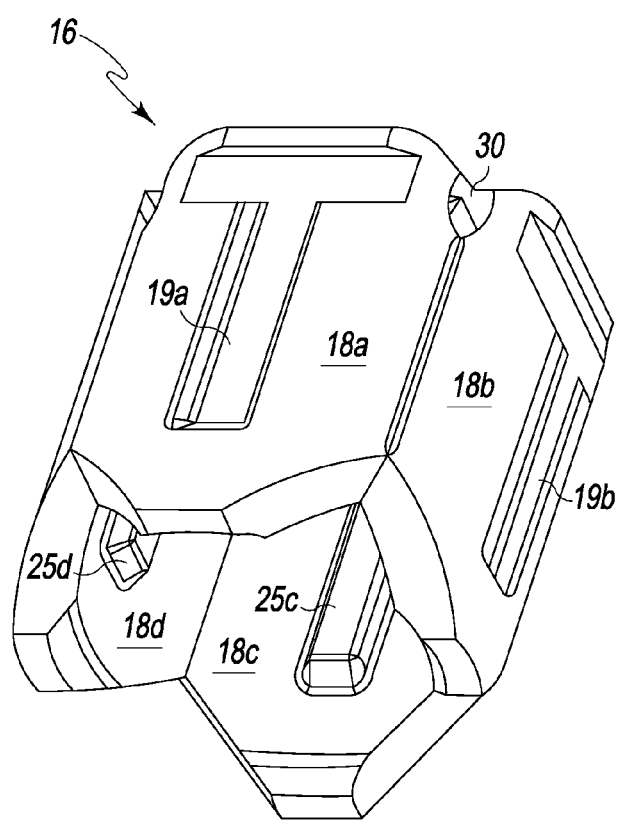
FIG. 11 is a perspective view of the plate component of FIG. 9 in a folded or compressed position.

FIGS. 4 through 8 depict the expanded spinous process spacer 10 as seen in FIGS. 1-3. FIGS. 9 through 11 depict a single plate 16 only of the spinous process spacer 10. As seen in FIGS. 9-11, each plate 16 has a core or base 32 defining a central portion or hub with a bore 34 extending through the base 32. While the base 32 is shown as being rectangular it should be appreciated that the base may take other shapes as desired and/or is appropriate. The plate 16 further includes a plurality of flanges (panels, sections, portions, leaves, petals or the like) 18 that extend radially from the base 32. The plate 16 (and thus the implant 10) is shown with four (4) flanges 18a, 18b, 18c and 18d it being understood that the implant may have more or less flanges. Each flange 18 (i.e. flanges 18a, 18b, 18c and 18d) is connected to the base 32 via a hinge or hinge structure, which in this case is a resilient coupling of the flange to the base. Each resilient coupling is defined by a strip of the elastic material that extends from an edge of the base 32 to a flange 18. Each strip is reduced in thickness relative to the other portions of the implant and/or particularly is of a thickness that allows elastic bending thereof without breaking in order to form an elastic or resilient hinge. As seen in FIGS. 1 through 8, the hinges allow their respective flanges 18a, 18b, 18c and 18d to fold inward toward an axis of the base 32 to thereby define the compressed, closed or folded position.

The flanges may be formed so as to normally be in the uncompressed or open position wherein a biasing force (i.e. deformation bias) is necessary to move the flanges into the compressed, folded or closed position. Once the deformation bias is removed, the closed position of the implant 10 automatically (e.g. through the elasticity of the material or the application of an external biasing force) becomes the deployed, uncompressed, expanded or open position. The flanges may alternatively be formed so as to normally be in the compressed or closed position wherein a biasing force (i.e. opening bias or force) is necessary to move the flanges into the open position.

Each plate 16 is configured to engage a like, adjacent plate 16. The configuration of a plate 16 provides for rotational stability of one plate 16 relative to an adjacent plate 16 and the positive axial joining thereof. Particularly, each flange 18 is configured to engage the like, adjacent flange 18 of the adjacent plate 16. The configuration of a flange 18 provides for rotational stability of one flange 18 relative to an adjacent flange 18 and the positive axial joining thereof. It should be appreciated that the configurations of the plate 16 and flanges 18 may differ from that shown in the figures.

Each flange 18 may include a curved concave inner surface and a curved convex outer surface. A ridge 25 (i.e. 25a, 25b, 25c and 25d) is formed on each inner surface. The flange ridge 25 extends radially from the base 32 and along the inner surface thereof. A channel 19 (i.e. 19a, 19b, 19c and 19d) is formed on each outer surface and is configured to receive a flange ridge 25 of an adjacent flange 18. It should be appreciated that the configuration of each flange 18 may change. Different configurations are contemplated.

With reference again to FIGS. 4 through 8, the spinous process spacer 10 is shown in the expanded position. The end cap 20 is held in frictional engagement with the post 24 via four (4) spokes 27a, 27b, 27c and 27d extending from a ring 26. The post 24 has a side for each spoke 27. This may not necessarily be the case. The ends of the four (4) spokes 27 are in frictional engagement with respective four (4) sides of the post 24. The post may have more or less sides as is the case with the number of spokes. In a different configuration, the post 24 is rectangular and the number of spokes is three (3).

The bottom end cap 22 defines a generally cup-shaped body 23 that holds the post 24 (i.e. the bottom end cap 22 is fixed relative to the post 24). The top end cap 20 is movable relative to the post 24. As the top end cap 20 is moved axially down the post 24 the top end cap 24 pushes against the top compressed plate 16. This, in turn, pushes against an adjacent plate 16 until an adjacent plate 16 pushes against a bottom-most plate 16. As the bottom-most plate 16 pushes against the bottom end cap 22, the compressed plates 16 expand.

It should be appreciated that the spinous process spacer 10 may come in various sizes/dimensions to accommodate various bony structure anatomies as well as provide a desired spacing therebetween. Also, the body of the present spinous process spacer 10 may be otherwise shaped.

The present spinous process spacer 10 is implanted between adjacent bony protrusions through an incision made in the patient proximate the area of implantation. Adjacent vertebrae are distracted and an appropriate dimensioned spinous process spacer 10 is situated between adjacent bony structures. The spinous process spacer 10 is inserted between the desired bony structures of adjacent vertebrae in the collapsed, closed or compressed position. Once in the desired location, the implant 10 is deployed into the expanded, open or un-compressed position in order to maintain space between the bony structures. The amount of space is determined by the dimensions of the implant 10. Because the implant 10 is introduced into the implant site in a compressed state and then expanded in situ, the implant 10 provides a smaller profile upon introduction of the implant than would an un-compressed implant. The smaller implant profile translates into use of the implant in minimally invasive surgery. It also provides other surgical benefits.

While the invention has been illustrated and described in detail in the drawings and foregoing description, the same is to be considered as illustrative and not restrictive in character, it being understood that only a preferred embodiment has been shown and described and that all changes and/or modifications that come within the spirit of the invention are desired to be protected.

What is claimed is:

1. A spinal implant for maintaining a desired spatial relationship between adjacent vertebrae of a spine, the spinal implant comprising:

a body defining a first profile when in a collapsed state during implantation of the spinal implant into a spinal implantation site between adjacent vertebrae, and a second profile when in an expanded state at the spinal implantation site between the adjacent vertebrae, the first profile being smaller than the second profile, and the expanded state forming a first area for receiving a first bony portion of a first vertebra of the adjacent vertebrae and a second area for receiving a second bony portion of a second vertebra of the adjacent vertebra, wherein the body comprises a plurality of stacked plates, each plate comprising a center section, a rectangular bore in the center section, and a plurality of flanges extending from the center section; and an expansion assembly releasably connected to the body and configured to expand the body from the collapsed state to the expanded state, the expansion assembly comprising:

a rod slidably extending through the rectangular bore in the center section of each plate, the rod having a plurality of planar sides defining a rectangular cross-section;

a first plate retention component at a first end of the rod and abutting the center section of a plate of the plurality of stacked plates that is at a first end of the plurality of stacked plates; and a second plate retention component axially slidably connected to a second end of the rod and abutting the center section of a plate of the plurality of stacked plates that is at a second end of the plurality of stacked plates, the second plate retention component having a rectangular bore to receive the rod;

whereby pulling the rod through the second plate retention component when the body is in the collapsed state expands the body toward the expanded state;

wherein the rod includes a longitudinal axis and the plurality of planar sides of the rod are parallel to the longitudinal axis, wherein the second plate retention component includes a ring and a plurality of spokes extending from the ring, wherein the second plate retention component is held in a releasable frictional engagement with the rod via the plurality of spokes;

wherein the plurality of flanges on each plate are pivotally connected to its center section;

wherein the plurality of flanges comprises four flanges and each one of the plurality of flanges is pivotally connected to the center section via a hinge;

wherein each plate defines a box shape when the body is in the collapsed state, and defines an X shape when the body is in the expanded state;

wherein each flange of each plate has a ridge on a first side and a channel on a second side, whereby the ridge of the flange of a plate engages the channel of a flange of an adjoining plate.

2. The spinal implant of claim 1, wherein the first area comprises a spinous process reception area for the first vertebra, and the second area comprises a spinous process reception area for the second vertebra.

3. The spinal implant of claim 1, wherein the first plate retention component comprises a cup shaped body that receives the first end of the rod and is fixed relative to the rod.

4. A spinal implant for maintaining a desired spatial relationship between adjacent vertebrae of a spine, the spinal implant comprising:
a body having a collapsed state during implantation of the spinal implant into a spinal implantation site between adjacent vertebrae, and an expanded state at the spinal implantation site between the adjacent vertebrae, the collapsed state defining a generally annular profile, and the expanded state defining a first area for receiving a first bony portion of a first vertebra of the adjacent vertebrae and a second area for receiving a second bony portion of a second vertebra of the adjacent vertebra, wherein the body comprises a plurality of stacked plates, each plate comprising a center section, a rectangular bore in the center section, and a plurality of flanges extending from the center section; and
an expansion assembly releasably connected to the body and configured to expand the body from the collapsed state to the expanded state, the expansion assembly comprising:
a rod slidably extending through the rectangular bore in the center section of each plate, the rod having a first end, a second end, and a plurality of planar sides defining a rectangular cross-section;
a first plate retention component axially slidably connected to the second end of the rod and abutting the center section of a plate of the plurality of stacked plates that is at a second end of the plurality of stacked plates, the first plate retention component having a ring and a plurality of spaced-apart spokes extending from the ring, wherein the first plate retention component is retained relative to the rod by the plurality of spokes in direct frictional engagement with the plurality of planar sides of the rod;
whereby pulling the rod through the second plate retention component when the body is in the collapsed state expands the body toward the expanded state.

5. The spinal implant of claim 4, wherein the first area comprises a spinous process reception area for the first vertebra, and the second area comprises a spinous process reception area for the second vertebra.

6. The spinal implant of claim 5, wherein the body comprises a plurality of adjoining plates.

7. The spinal implant of claim 6, wherein each plate of the plurality of adjoining plates comprises:
a plurality of flanges pivotally connected to the center section.

8. The spinal implant of claim 7, wherein the plurality of flanges comprises four flanges and each one of the plurality of flanges is pivotally connected to the center section via a hinge.

9. The spinal implant of claim 8, wherein each plate defines a generally annular shape when the body is in the collapsed state, and an X shape when the body is in the expanded state.

10. The spinal implant of claim 9, wherein the expansion assembly comprises:
a second plate retention component attached to one end of the rod and abutting the center section of a plate of the plurality of adjoining plates that is at a first end of the plurality of adjoining plates.

11. The spinal implant 10, wherein each flange of each plate has a ridge on a first side and a channel on a second side, whereby the ridge of the flange of a plate engages the channel of the flange of an adjoining plate.

12. A spinous process spacer for maintaining a desired spatial relationship between adjacent vertebrae of a spine, the spinal implant comprising:
a plurality of adjoining plates, each one of the plurality of adjoining plates having a center section, a rectangular bore in the center section, and a plurality of flanges pivotally connected to the center section, the plurality of adjoining plates defining a collapsed state during implantation of the spinal implant into a spinal implantation site between adjacent vertebrae and an expanded state at the spinal implantation site between the adjacent vertebrae, the collapsed state defining a generally annular profile and the expanded state defining a first area for receiving a spinous process of a first vertebra of the adjacent vertebrae and a second area for receiving a spinous process of a second vertebra of the adjacent vertebra;
an expansion assembly connected to the plurality of adjoining plates and configured to expand the plurality of adjoining plated from the collapsed state to the expanded state, the expansion assembly comprising:
a rod slidably extending through the rectangular bore in the center section of each plate, the rod having a first end, a second end, a longitudinal axis, and a plurality of planar sides parallel to the longitudinal axis and defining a rectangular cross-section;
a first plate retention component at a first end of the rod and abutting the center section of a plate of the plurality of stacked plates that is at a first end of the plurality of stacked plates, the first plate retention component comprises a cup shaped body that receives the rod; and
a second plate retention component slidably connected to a second end of the rod and abutting the center section of a plate of the plurality of stacked plates that is at a second end of the plurality of stacked plates, the second plate retention component having a ring and a plurality of inwardly projecting spokes extending from the ring and spaced apart from adjacent spokes, wherein the first plate retention component is retained relative to the rod by the plurality of spokes in frictional engagement with the plurality of planar sides of the rod;
whereby pulling the rod through the second plate retention component when the body is in the collapsed state expands the body toward the expanded state;
wherein each flange of each plate has a ridge on a first side and a channel on a second side, whereby the ridge of the flange of a plate engages the channel of the flange of an adjoining plate.

13. The spinous process spacer of claim 12, wherein the plurality of flanges comprises four flanges and each one of the plurality of flanges is pivotally connected to the center section via a hinge.

14. The spinous process spacer of claim 12, wherein the ring abuts against a flat portion on each flange adjacent the channel.

* * * * *